United States Patent [19]
Gras

[11] Patent Number: 5,847,067
[45] Date of Patent: Dec. 8, 1998

[54] URETDIONE-FUNCTIONAL POLYISOCYANATES, A PROCESS FOR THEIR PREPARATION, AND THEIR USE

[75] Inventor: Rainer Gras, Bochum, Germany

[73] Assignee: Huels Aktiengesellschaft, Marl, Germany

[21] Appl. No.: 927,319

[22] Filed: Sep. 11, 1997

[30] Foreign Application Priority Data

Sep. 13, 1996 [DE] Germany .................. 196 37 375.1

[51] Int. Cl.$^6$ ...................... C08G 18/81; C07G 229/00
[52] U.S. Cl. ................... 528/45; 540/202; 524/86; 528/44; 528/68; 528/73; 528/87; 528/110
[58] Field of Search ............... 524/86; 540/202; 528/44, 45, 68, 73, 87, 110

[56] References Cited

U.S. PATENT DOCUMENTS

| | | | |
|---|---|---|---|
| 3,943,158 | 3/1976 | Dietrich et al. ............ | 564/32 |
| 4,520,186 | 5/1985 | Hess et al. ................ | 528/73 |
| 4,668,780 | 5/1987 | Disterldorf et al. ........ | 540/202 |
| 5,216,107 | 6/1993 | Pedain et al. ............. | 528/45 |

FOREIGN PATENT DOCUMENTS

| | | |
|---|---|---|
| 0 045 998 | 2/1982 | European Pat. Off. . |
| 195 46 750 | 6/1997 | Germany . |

*Primary Examiner*—Yogendra N. Gupta
*Attorney, Agent, or Firm*—Oblon, Spivak, McClelland, Maier & Neustadt, P.C.

[57] ABSTRACT

Urea- and uretdione-functional polyisocyanates having the following formula (I):

$$Y-R-N\underset{\underset{O}{\overset{\|}{C}}}{\overset{\overset{O}{\overset{\|}{C}}}{\diamond}}N- \quad (I)$$

-continued $$\left[-R-NH-\overset{O}{\overset{\|}{C}}-\underset{R^1}{\overset{|}{N}}-R^2-\underset{R^3}{\overset{|}{N}}-\overset{O}{\overset{\|}{C}}-NH-R-N\underset{\underset{O}{\overset{\|}{C}}}{\overset{\overset{O}{\overset{\|}{C}}}{\diamond}}N\right]_n-R-Y$$

where

Y is $-NCO$, or $-NH-\overset{O}{\overset{\|}{C}}-B$

B is $-\underset{H}{\overset{|}{N}}-R^4$, $-N\underset{R^5}{\overset{R^4}{\diamond}}$, $-OR^4$, or an N-substituted caprolactam ring, $R^4 = N-O-$ or 1,2,4-triazole;

R is $$\begin{array}{c} H_3C \\ H_3C \end{array} \diamond \begin{array}{c} CH_3 \\ CH_2- \end{array}$$

n is an integer of from 1 to 20;

$R^1$, $R^3$ = not more than one linear or branched (cyclo)alkyl radical having 1–14 carbon atoms or H and at least one of the formula:

$$R^4-O\overset{\|}{\underset{O}{C}}-CH_2-\overset{|}{CH}-\overset{\|}{\underset{O}{C}}-OR^4 \text{ or}$$

$$R^4-O-\overset{\|}{\underset{O}{C}}-CH_2-CH_2-$$

$R^2 = R$, linear or branched (cyclo)alkyl radical having 6 carbon atoms;

$R^4$, $R^5$ = identical or different hydrocarbon radicals having 1 to 14 carbon atoms.

9 Claims, No Drawings

URETDIONE-FUNCTIONAL POLYISOCYANATES, A PROCESS FOR THEIR PREPARATION, AND THEIR USE

BACKGROUND OF THE INVENTION

1. Field of the Invention

The invention relates to uretdione-functional polyisocyanates (i.e. containing uretdione groups) having free, partially or totally blocked isocyanate groups; to a preparation process and to a method of use of the uretdione-functional polyisocyanates for the preparation of polyurethane (PU) coating systems, especially PU powder coatings; and to the preparation of reduced gloss coatings.

2. Discussion of the Related Art

There has been increasing interest in recent years in powder coatings with reduced gloss. The reason for this is mainly practical; glossy surfaces require a far greater level of cleaning than do matt surfaces. Furthermore, it may be necessary for safety reasons to avoid strongly reflecting surfaces.

The simplest solution for obtaining a surface with reduced gloss is to add greater or lesser amounts of filler such as chalk, barium sulfate or finely divided silica to the powder coating formulations depending on the desired degree of gloss, known as the matt effect. These additives or auxiliaries lead, however, to a reduction in technical film properties such as flexibility, Erichsen indentation, ball impact strength, adhesion and chemical resistance.

The addition of substances which are incompatible with the coating material, such as waxes or cellulose derivatives, for example, does indeed bring about matting, however, slight changes in the course of extrusion lead to fluctuations in the surface gloss. The reproducibility of the matt effect is not ensured.

Surprisingly it has been possible to develop a PU powder coating with reduced gloss which is not hampered by the disadvantages of the prior art. This has been achieved by employing crosslinkers which are reaction products of isophorone diisocyanate uretdione (IPDI-UD) and disecondary diamines.

SUMMARY OF THE INVENTION

The present invention therefore provides urea- and uretdione-functional polyisocyanates having free, partially or totally blocked isocyanate groups, of the following formula (I):

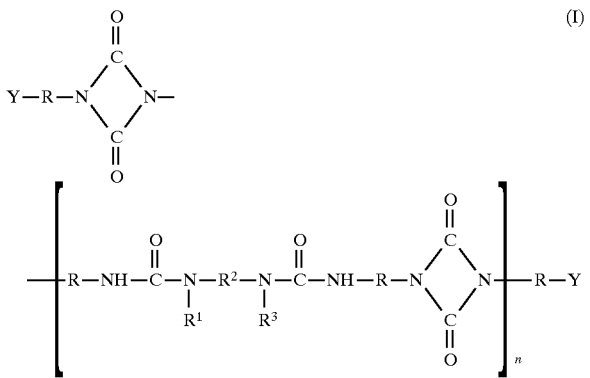

where

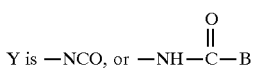

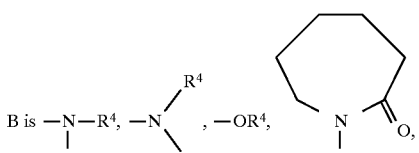

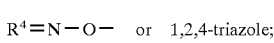

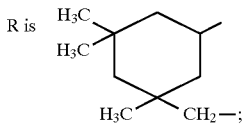

n is an integer of from 1 to 20;

$R^1$, $R^3$ = not more than one linear or branched (cyclo)alkyl radical having 1–14 carbon atoms or H and at least one of the formula

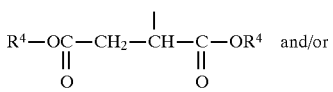

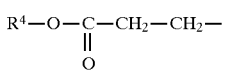

$R^2 = R$, linear or branched (cyclo)alkyl radical having 6 carbon atoms;

$R^4$, $R^5$ = identical or different hydrocarbon radicals having 1 to 14 carbon atoms.

The novel polyisocyanates are characterized by a) a content of free NCO groups of $\leq 5\%$, preferably $\leq 4$, in particular $\leq 2\%$ by weight, b) an overall NCO content (free and latent and/or blocked) of from 8 to 16%, preferably from 9 to 15%, in particular from 10 to 14% by weight, and c) a melting range which varies within wide limits, from 70° to 180° C.

The polyurethanes of the present invention are outstandingly suitable for the preparation of PU powder coatings with reduced gloss.

DESCRIPTION OF THE PREFERRED EMBODIMENTS

It is an object of the present invention to provide a urea and uretdione-functional polyisocyanate having free, or partially or totally blocked isocyanate groups of the following formula (I):

-continued

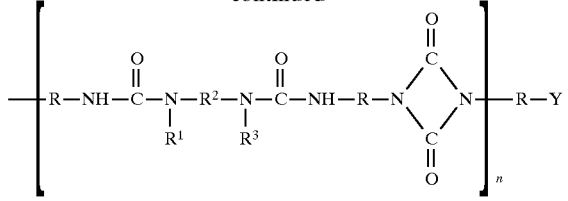

where
Y, B, R, $R^1$, $R^2$, $R^3$ and n are as described above.

The novel polyisocyanates are characterized by a) a content of free NCO groups of $\leq 5\%$, preferably $\leq 4$, in particular $\leq 2\%$ by weight,

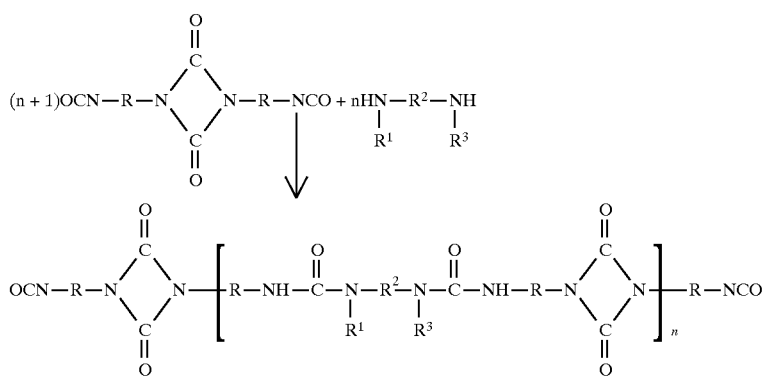

(I)

b) an overall NCO content (free and latent and/or blocked) of from 8 to 16%, preferably from 9 to 15%, in particular from 10 to 14% by weight, and c) a melting range which varies from 70° to 180° C.

It is an additional object of the present invention to provide a process for preparing the novel urea- and uretdione-functional polyisocyanates having free, or partially or totally blocked isocyanate groups, in accordance with the following equation:

The free NCO groups of (I) can, if desired, be reacted partially or totally with the blocking agent (B) described above.

The uretdione to be employed in the novel process is the IPDI (isophorone diisocyanate) uretdione as described in DE-A 30 30 513 and DE-A 37 39 549, having a free NCO content of 16.8–18.5%; in other words, there must be more or less high proportions of polyuretdione (IPDI) in the reaction product. The monomer content is $\leq 1\%$. The overall NCO content of the IPDI uretdione after heating at 180°–200° C. (0.5 h) is 37.4–37.8%.

The secondary diamines employed for the novel process have long been known and are obtained by reacting primary diamines $H_2N$—$R^2$—$NH_2$ with maleic or fumaric esters, reacting 0.5 mol of diamine in a known manner per mole of maleic or fumaric ester. The diamines $H_2N$—$R^2$—$NH_2$ are aliphatic and/or (cyclo)aliphatic diamines, such as 1,2-diaminoethane, 1,3-diaminopropane, 1,4-diaminobutane, 1,5-diaminopentane, 1,6-diaminohexane, 2-methyl-1,5-diaminopentane (DA 51), 2,2,4(2,4,4)-trimethyl-1,6-diaminohexane (TMD), 2,4'- and/or 4,4'-diaminodicyclohexylmethane (HMDA), 1,11-diaminoundecane, 1,12-diaminododecane, 1,4- and/or 1,2-diaminocyclohexane, m-hexahydroxylylenediamine (HXDA), and 1-amino-3,5,5-trimethyl-5-aminomethylcyclohexane (isophoronediamine, abbreviated to IPD). From the large number of known maleic and fumaric esters, those principally used have been diethyl, dibutyl and di-2-ethylhexyl maleate.

An advantageous variant of the preparation of the novel polyisocyanates is represented by disecondary diamines which are obtained by reacting a primary amino group with an abovementioned maleic or fumaric ester-, in other words, one mole of maleic ester is reacted per mole of primary diamine, and then the second amino group is made secondary using an acrylic ester such as methyl, ethyl, butyl, t-butyl or 2-ethylhexyl acrylate. The reaction takes place at between 60° and 80° C. The reaction of the amino groups with maleic or fumaric ester and acrylic ester can of course also be carried out in the reverse order.

A further variant of preparing the novel polyisocyanates is represented by the reaction of diamines containing a secondary and primary amino group with maleic or fumaric ester or acrylic ester, the primary amino group being made secondary.

In some cases it has proven expedient to block the free NCO groups of the uretdione-functional polyaddition products. Where the NCO groups are blocked irreversibly, i.e. the blocking agent is not eliminated during the stoving procedure, the free NCO groups of uretdione-diamine adduct are reacted with monoalcohols, for example methanol, ethanol, butanol, 2-ethylhexanol (EHL), or with secondary monoamines, such as dibutylamine (DBA), di-2-ethylhexylamine, or methylcyclohexylamine. For the reversible blocking of the free NCO groups, ketoximes such as acetone oxime, methyl ethyl ketoxime, acetophenone oxime and cyclohexanone oxime, lactams such as caprolactam, and triazoles such as 1,2,4-triazole are employed.

The novel uretdione-functional polyaddition compounds are prepared by the process which will now be elucidated. Preparation takes place such that n+1 mol of IPDI uretdione are reacted with n mol of disecondary diamine, with the temperature not exceeding 40° C. In accordance with the invention the free NCO groups can be reacted with blocking agents prior to or following the reaction with the disecondary diamines.

Reaction can in each case take place with or without solvent. Where a solvent is employed, it can be selected from the group consisting of aromatic hydrocarbons, esters or ketones, for example toluene, ethyl acetate or butyl acetate, acetone, methyl ethyl ketone, methyl isobutyl ketone, and any desired mixtures of these solvents. Acetone is a preferred solvent.

In one preferred embodiment the novel compounds are prepared by metering the disecondary diamine at room temperature into the acetonic solution of the IPDI uretdione at a rate such that the temperature of the reaction solution does not exceed 40° C. After the end of the addition of diamine, the reaction is at an end. The acetone is distilled off, if the reaction product is to include free NCO groups. If, however, the reaction product is no longer to include free NCO groups, reaction with the blocking agent follows at about 60° C. If alcohols are employed as blocking agents, it has proven expedient to react IPDI uretdione at about 70° C. with alcohols, in the absence of solvent, and, once OH/NCO reaction has taken place at room temperature, to carry out the reaction with the disecondary diamine in acetone. If solvent is not used, the reaction takes place continuously in an intensive compounding apparatus, preferably using a twin-screw extruder.

It often appears expedient to accelerate the course of the reaction, especially for preparing the novel partially or totally blocked polyisocyanates. Suitable catalysts are organotin compounds, such as Sn(II) octoate, dibutyltin dilaurate (DBTL), tin maleate, etc., which are added in proportions of from 0.01 to 0.5% by weight, preferably from 0.03 to 0.15% by weight.

The present invention also provides for the use of the urea- and uretdionefunctional polyisocyanates for preparing polyurethane coating systems, especially in combination with hydroxyl-containing polymers and/or with the additives which are customary in PU chemistry, for preparing transparent and pigmented PU powder coatings. Suitable co-reactants for PU powder coatings are compounds carrying functional groups which, during the curing process, react with isocyanate groups as a function of temperature and time, examples being hydroxyl, carboxyl, mercapto, amino, urethane and (thio)urea groups. Polymers which can be employed are addition polymers, condensation polymers and polyaddition compounds.

In principle it is possible to use any polymer containing more than two OH groups and melting at at least 70° C. These are polyetherpolyols, polyesteramidepolyols, polyurethanepolyols, hydroxylated acrylate resins, etc., whose OH groups are intended for crosslinking with the novel uretdionefunctional polyisocyanates. Among the numerous possibilities for hydroxyl containing polymers, particular preference is given in the context of the present invention to polyesterpolyols. The hydroxyl-containing polyesters employed with particular preference have an OH functionality of >2, an OH number of from 20 to 200 mg of KOH/g, preferably from 30 to 150 mg of KOH/g, a viscosity at 160° C. of <60,000 mPa.s, preferably <40,000 mPa.s, and a melting point of from between 70° and 120° C., preferably from 75° to 100° C.

Polyesters of this kind can be obtained in a manner known per se by condensation in an inert-gas atmosphere at temperatures from 100° to 260° C., preferably from 130° to 220° C., in the melt or by an azeotropic procedure, as is described in "Methoden der Organischen Chemie" (Houben-Weyl), vol. 14/2, 1–5, 21–23, 40–44, Georg Thieme Verlag, Stuttgart, 1963 or in C. R. Martens, "Alkyd Resins" 51–59, Reinhold Plastics Appl. Series, Reinhold Publishing Comp., New York, and in DE-A 19 57 483, DE-A 25 42 191, DE-A 30 04 876 and DE-A 31 43 060.

The mixing ratio of the hydroxyl-containing polymers to the novel polyisocyanates is generally chosen such that there is 0.5–1.2, preferably 0.8–1.1, more preferably 1.0, NCO group per OH group.

In order to raise the gelling rate of the heat-curable a powder coatings it is possible to add a catalyst. Catalysts used are organotin compounds such as dibutyltin dilaurate (DBTL), Sn(II) octoate, dibutyltin maleate, etc. The amount of catalyst added is 0.1–5 parts by weight per 100 parts by weight of the hydroxyl-containing polyester.

For the preparation of PU powder coatings, the isocyanate component is mixed with the appropriate hydroxyl-containing polymers and, if desired, a catalyst and also a pigment and a customary auxiliary such as a filler and a leveling agent, for example silicone oil, acrylate resins, and the mixture is homogenized in the melt. This can be carried out in appropriate apparatus, for example heatable compounders, but preferably by extrusion, in which case upper temperature limits of from 130° to 140° C. should not be exceeded. The extruded mass is cooled to room temperature, comminuted appropriately and then ground to form the ready-to-spray powder. The ready-to-spray powder can be applied to appropriate substrates in accordance with the known techniques, for example by electrostatic powder spraying, fluidized bed sintering and electrostatic fluidized-bed sintering. Following the application of the powder the coated workpieces are cured by heating them for from 30 to 10 minutes at a temperature of from 180° to 220° C.

The specification and following Examples are also present in priority document, German Patent Application 196 37 375.1 which is incorporated herein by reference.

Having generally described this invention, a further understanding can be obtained by reference to certain specific examples which are provided herein for the purpose of illustration only and are not intended to be limiting unless otherwise specified.

EXAMPLES

A. Preparation of Diamines

I. Reaction products of 1 mol of diamine and 2 mol of maleic ester

General preparation procedure 1 mol of diamine is added dropwise at 50°–60° C. to 2 mol of maleic or fumaric ester at a rate such that the temperature of the reaction mixture does not exceed 70° C. After the diamine has been added, a reaction is completed by continuing heating at 60° C. for about 2 h more. No further treatment (distillation) of the reaction mixture is necessary for the subsequent reaction with the polyisocyanate.

TABLE 1

| Example A I. | Composition | | Amine number |
|---|---|---|---|
| | Diamine (1 mol) | Maleic acid (MA) ester (2 mol) | [mg of KOH/g] |
| 1 | IPD | MA diethyl ester | 210 |
| 2 | IPD | MA dibutyl ester | 175 |
| 3 | IPD | MA di-2-ethylhexyl ester | 124 |
| 4 | TMD | MA diethyl ester | 217 |
| 5 | TMD | MA dibutyl ester | 175 |
| 6 | H₂N—CH₂—⬡—CH₂—NH₂ | MA diethyl ester | 227 |
| 7 | H₂N—CH₂—⬡—CH₂—NH₂ | MA dibutyl ester | 181 |
| 8 | H₂N—⬡—CH₂—⬡—NH₂ | MA diethyl ester | 196 |
| 9 | H₂N—⬡—CH₂—⬡—NH₂ | MA dibutyl ester | 160 |

IPD: isophorone diisocyanate
TMD: 2,2,4 (2,4,4,)-trimethyl-1,6-diaminohexane
MA: maleic acid II. Reaction products of 1 mol of diamine and 1 mol of maleic ester and 1 mol of acrylic ester General preparation procedure 1 mol of acrylic ester is added dropwise at 60°–70° C. to 1 mol of diamine at a rate such that the temperature of the reaction mixture does not exceed 80° C. After the acrylic ester has been added, heating is continued at 70° C. until the amine content has reached the calculated value. Then 1 mol of maleic or fumaric ester is added dropwise at 50°–60° C. at a rate such that the temperature of the reaction mixture does not exceed 70° C. After the maleic ester has been added, the reaction is completed by continuing heating at 70° C. for about 2 h or more. No further treatment (distillation) of the reaction mixture is necessary for the subsequent reaction with polyisocyanate.

TABLE 2

| | Composition (each of 1 mol) | | | |
|---|---|---|---|---|
| Example A II. | Diamine | MA ester | Acrylic acid (AA) ester | Amine number [mg of KOH/g] |
| 1 | IPD | diethyl ester | AA ethyl ester | 251 |
| 2 | IPD | dibutyl ester | AA methyl ester | 230 |
| 3 | TMD | diethyl ester | AA t-butyl ester | 241 |
| 4 | TMD | dibutyl ester | AA methyl ester | 236 |
| 5 | DA 51 | diethyl ester | AA methyl ester | 295 |
| 6 | HMDA | diethyl ester | AA ethyl ester | 231 |
| 7 | HMDA | dihexyl ester | AA methyl ester | 191 |
| 8 | HXDA | diethyl ester | AA ethyl ester | 267 |

AA: acrylic acid
MA: maleic acid
IPD: isophorone diamine
TMD: 2,2,4(2,4,4)-trimethyl-1,6-diaminohexane
DA51: 2-methyl-1,5-diaminopentane
HMDA: 4,4'-diaminodicyclohexylmethane
HXDA: m-hexahydroxylylenediamine III. Reaction products of 1 mol of diamine and 1 mol of maleic or fumaric ester General preparation procedure 1 mol of maleic or fumaric ester is added at 50°–60° C. to 1 mol of diamine at a rate such that the reaction temperature does not exceed 70° C. After the ester has been added, heating is continued at 60° C. for about 1 h more. After cooling, the reaction product can be used for the reaction with polyisocyanate uretdione.

TABLE 3

| Example A III. | Composition Diamine (1 mol) | Maleic acid (MA) ester (1 mol) | Amine number [mg of KOH/g] |
|---|---|---|---|
| 1 | IPD | MA diethyl ester | 324 |
| 2 | IPD | MA dibutyl ester | 280 |
| 3 | IPD | MA di-2-ethylhexyl ester | 218 |
| 4 | TMD | MA diethyl ester | 336 |
| 5 | TMD | MA dibutyl ester | 289 |
| 6 | 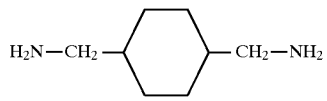 H₂N—CH₂—⬡—CH₂—NH₂ | MA diethyl ester | 355 |
| 7 | H₂N—CH₂—⬡—CH₂—NH₂ | MA dibutyl ester | 301 |
| 8 |  H₂N—⬡—CH₂—⬡—NH₂ | MA diethyl ester | 290 |
| 9 | H₂N—⬡—CH₂—⬡—NH₂ | MA dibutyl ester | 255 |

IPD: isophorone diamine
TMD: 2,2,4 (2,4,4,)-trimethyl-1,6-diaminohexane
MA: maleic acid B Preparation of the novel compounds General preparation procedure The diamine of Table 1 to 3 is metered with intense stirring at room temperature into the acetonic solution of the IPDI uretdione at a rate such that the temperature of the reaction solution does not exceed 40° C. After the diamine has been added the reaction is virtually at an end, and the acetone is removed. Where it is intended that the free NCO groups of the IPDI uretdione/diamine addition product (molar ratio: IPDI uretdione/diamine=(n+1)/n) are to be blocked with secondary monoamines, then the procedure, following the IPDI uretdione/diamine reaction, is to add the blocking agent in portions at about 40° C. and to continue heating at 60° C. for about 1 h. Then the acetone is removed. Where the free NCO groups of the IPDI uretdione/diamine addition product are to be blocked with alcohols (HO-R⁴), then the following procedure has proven advantageous:

a) the IPDI uretdione was reacted with the alcohol in bulk at about 70° C. (0.5 h), b) subsequently was cooled and dissolved in acetone, and c) this acetone solution was reacted with the diamine.

The IPDI uretdione employed had the following characteristics:

NCO content (free): 16.8–18.5% by weight

NCO content (total): 37.4–37.8% by weight

The novel urea- and uretdione-functional polyisocyanates listed in the Tables below were synthesized in accordance with the general preparation procedure.

TABLE 4

Urea- and uretdione-functional polyisocyanates

| | Composition in mol | | | | Chemical and physical data | | | |
|---|---|---|---|---|---|---|---|---|
| Example B | IPDI uretdione | Diamine from Table 1 | Blocking Agent DBA | EHL | NCO content [% by wt.] free | total | Melting range [°C.] | Glass transition temperature [°C.] |
| 1 | 3 | AI.1.(2) | — | — | 3.3 | 14.7 | 108–110 | 73–84 |
| 2 | 3 | AI.1. (2) | 1 | — | 1.5 | 12.4 | 115–118 | 77–93 |
| 3 | 5 | AI.1. (4) | — | — | 1.8 | 12.3 | 133–137 | 79–90 |
| 4 | 6 | AI.1. (5) | — | — | 1.3 | 12.0 | 138–141 | 81–93 |
| 5 | 6 | AI.1. (5) | 1.7 | — | 0.2 | 10.5 | 143–146 | 84–97 |
| 6 | 9 | AI.1. (8) | — | — | 0.9 | 11.0 | 153–156 | 120–131 |
| 7 | 15 | AI.1. (14) | — | — | 0.4 | 10.3 | 161–163 | 117–136 |
| 8 | 15 | AI.1. (14) | — | 1.8 | <0.1 | 9.6 | 163–168 | 121–133 |

TABLE 4-continued

Urea- and uretdione-functional polyisocyanates

| Example B | IPDI uretdione | Diamine from Table 1 | Blocking Agent DBA | Blocking Agent EHL | NCO content [% by wt.] free | NCO content [% by wt.] total | Melting range [°C.] | Glass transition temperature [°C.] |
|---|---|---|---|---|---|---|---|---|
| 9 | 4 | AI.2. (3) | — | — | 2.0 | 12.0 | 90–93 | 56–76 |
| 10 | 6 | AI.2. (5) | — | — | 1.1 | 10.9 | 108–112 | 70–80 |
| 11 | 10 | AI.2. (9) | — | — | 0.6 | 9.9 | 153–157 | 111–121 |
| 12 | 10 | AI.2. (9) | 1.8 | — | <0.1 | 8.9 | 157–161 | 118–133 |
| 13 | 5 | AI.4. (4) | — | — | 1.8 | 12.3 | 96–98 | 57–73 |
| 14 | 8 | AI.4. (7) | — | — | 1.0 | 11.4 | 129–133 | 100–114 |
| 15 | 6 | AI.5. (5) | — | — | 1.3 | 10.9 | 78–80 | 43–55 |
| 16 | 9 | AI.5. (8) | — | — | 0.7 | 10.0 | 133–136 | 76–97 |
| 17 | 5 | AI.6. (4) | — | — | 2.0 | 11.9 | 138–141 | 92–104 |
| 18 | 6 | AI.6. (5) | — | 1.5 | 0.1 | 10.1 | 140–144 | 91–105 |
| 19 | 4 | AI.7. (3) | — | — | 2.0 | 11.6 | 126–128 | 66–78 |
| 20 | 6 | AI.7. (5) | — | — | 1.0 | 10.1 | 133–136 | 87–98 |
| 21 | 4 | AI.8. (3) | — | — | 2.2 | 13.6 | 112–114 | 73–89 |
| 22 | 4 | AI.8. (3) | 1.5 | — | 0.4 | 11.0 | 117–121 | 76–90 |
| 23 | 6 | AI.8. (5) | — | — | 1.5 | 12.3 | 112–114 | 77–89 |
| 24 | 8 | AI.8. (7) | — | — | 0.9 | 11.5 | 141–144 | 95–109 |
| 25 | 6 | AI.9 (5) | — | — | 1.3 | 11.1 | 89–92 | 46–47 |
| 26 | 10 | AI.9. (9) | — | — | 0.6 | 10.1 | 156–159 | 114–127 |

IPOI: isophorone diisocyanate
DBA: dibutylamine
EHL: 2-ethylhexanol

TABLE 5

Urea- and uretdione-functional polyisocyanates

| Example B | IPDI uretdione | Diamine from Table 2 | Blocking Agent DBA | Blocking Agent EHL | NCO content [% by wt.] free | NCO content [% by wt.] total | Melting range [°C.] | Glass transition temperature [°C.] |
|---|---|---|---|---|---|---|---|---|
| 1 | 5 | AII.1. (4) | — | — | 1.7 | 13.5 | 136–140 | 81–94 |
| 2 | 7 | AII.1. (6) | — | — | 1.1 | 12.4 | 147–151 | 93–109 |
| 3 | 6 | AII.2. (5) | 1.7 | — | <0.1 | 10.6 | 113–116 | 74–97 |
| 4 | 9 | AII.2. (8) | — | — | 0.8 | 11.6 | 147–151 | 95–111 |
| 5 | 6 | AII.3. (5) | — | — | 1.3 | 12.6 | 101–104 | 61–75 |
| 6 | 10 | AII.4. (9) | — | — | 0.6 | 11.5 | 140–142 | 86–97 |
| 7 | 12 | AII.5. (11) | — | — | 0.6 | 12.5 | 157–161 | 105–117 |
| 8 | 6 | AII.6. (5) | — | 1.8 | <0.1 | 10.7 | 143–145 | 114–129 |
| 9 | 8 | AII.6. (7) | — | — | 0.9 | 11.8 | 161–164 | 125–138 |
| 10 | 7 | AII.7. (6) | — | — | 0.9 | 11.0 | 134–137 | 77–94 |
| 11 | 5 | AII.8. (4) | 1.5 | — | 0.2 | 11.9 | 84–87 | 43–55 |
| 12 | 10 | AII.8. (9) | — | — | 0.7 | 12.2 | 158–161 | 117–130 |

IPDI: isophorone diisocyanate
DBA: dibutylamine
EHL: 2-ethylhexanol

TABLE 6

Urea- and uretdione-functional polyisocyanates

| Example B | IPDI | Diamine from Table 3 | Blocking Agent DBA | Blocking Agent EHL | NCO content [% by wt.] free | NCO content [% by wt.] total | Melting range [°C.] | Glass transition temperature [°C.] |
|---|---|---|---|---|---|---|---|---|
| 1 | 6 | AIII.1. (5) | — | — | 1.6 | 14.0 | 133–137 | 76–91 |
| 2 | 5 | AIII.2. (4) | 1.6 | — | 0.2 | 11.5 | 103–107 | 69–67 |
| 3 | 8 | AIII.2. (7) | — | — | 1.1 | 12.6 | 144–146 | 87–99 |
| 4 | 5 | AIII.4. (4) | — | — | 2.0 | 14.9 | 91–94 | 55–71 |
| 5 | 10 | AIII.4. (9) | — | — | 0.8 | 13.1 | 137–139 | 79–90 |
| 6 | 7 | AIII.5. (6) | — | — | 1.2 | 12.0 | 99–103 | 63–77 |
| 7 | 6 | AIII.6. (5) | — | 1.7 | 1.6 | 14.5 | 147–149 | 97–110 |
| 8 | 9 | AIII.6. (8) | — | — | 1.0 | 13.6 | 157–161 | 111–125 |
| 9 | 4 | AIII.7. (3) | 1.8 | — | 0.1 | 11.7 | 121–124 | 62–77 |
| 10 | 7 | AIII.8. (6) | — | — | 1.2 | 13.0 | 137–140 | 73–92 |
| 11 | 3 | AIII.8. (2) | — | 2.0 | 0 | 11.4 | 98–100 | 57–71 |
| 12 | 12 | AIII.9. (11) | — | — | 0.5 | 11.4 | 160–164 | 117–130 |

IPDI: isophorone diisocyanate
DBA: dibutylamine
EHL: 2-ethylhexanol

C Polyol component

General preparation procedure

The starting components—terephthalic acid (TA), dimethyl terephthalate (DMT), 1,6-hexanediol (HD), neopentylglycol (NPG), 1,4-dimethylolcyclohexane (DMC) and trimethylolpropane (TMP)—are placed in a reactor and heated with the aid of an oil bath. After the substances have largely melted, 0.5% by weight of di-n-butyltin oxide is added as catalyst at a temperature of 160° C. Initial elimination of methanol occurs at a temperature of around 170° C. Over the course of 6 to 8 hours the temperature is raised to 220°–230° C., and the reaction is taken to completion over the course of a further 12 to 15 hours. The polyester is cooled to 200° C. and substantially freed from volatile constituents by applying a vacuum (1.33 mbar) over the course of 30 to 45 minutes. Throughout the reaction period the bottom product is stirred and a gentle stream of $N_2$ is passed through the reaction mixture.

Table 7 shows polyester compositions with the corresponding physical and chemical data.

TABLE 7

Polyesters

| Example C | Starting components | | | | | | Chemical and physical data | | | | |
|---|---|---|---|---|---|---|---|---|---|---|---|
| | TA [mol] | DMT [mol] | HD [mol] | NPG [mol] | DMC [mol] | TMP [mol] | OH number [mg of KOH/g] | Acid number [mg of KOH/g] | m.p. [°C.] | DTA [°C.] | Viscosity at 160° C. [mPa · s] |
| 1 | 10 | 10 | 6.25 | 10.5 | 2 | 2.9 | 55–60 | 3–4 | approx. 75 | approx. 50 | ≈25,000 |
| 2 | 11 | 11 | 9.75 | 11.0 | — | 2.9 | 50–55 | 3–4 | approx. 75 | approx. 50 | ≈22,000 |

TA: terephthalic acid
DMT: dimethyl terephthalate
HD: 1,6-hexanediol
NPG: neopentylglycol
DMC: 1,4-dimethylolcyclohexane
TMP: trimethylolpropane
DTA: Differential Thermal Analysis D Polyurethane powder coatings General preparation procedure The comminuted products—urea- and uretdione-functional polyisocyanates (crosslinkers), polyesters, leveling agent masterbatch and, if desired, catalyst masterbatch, are intimately mixed, together if appropriate with the white pigment, in an edge runner mill and the mixture is then homogenized in an extruder at up to 130° C. After cooling, the extrudate is fractionated and ground with a pin mill to a particle size <100 pm. The powder thus prepared is applied using an electrostatic powder spraying unit at 60 kV to degreased, optionally pretreated iron panels, which are then stoved in a convection oven at temperatures between 180° and 200° C.

Leveling agent masterbatch

10% by weight of the leveling agent—a commercial copolymer of butyl acrylate and 2-ethylhexyl acrylate—are homogenized in the corresponding polyester in the melt and are comminuted after solidification.

Catalyst masterbatch

5% by weight of the catalyst—dibutyltin dilaurate (DBTL) are homogenized in the corresponding polyester in the melt and are comminuted after solidification.

The abbreviations in the following tables mean
LT=layer thickness in μm
EI=Erichsen indentation in mm (DIN 53 156)
CH=crosshatch test (DIN 53 151)
GG 60° ∢=Gardner gloss measurement (ASTM-D 5233)
Imp. rev.=impact reverse in g.m

TABLE 8

Pigmented powder coatings

| | Example D | | | | | | | | | | | |
|---|---|---|---|---|---|---|---|---|---|---|---|---|
| Formulation | 1[a] | 2[a] | 3[a] | 4[a] | 5[a] | 6[a] | 7[b] | 8[b] | 9[a] | 10[a] | 11[b] | 12[a] |
| Crosslinker acc. to B | 23.7 | 27.6 | 27.6 | 27.6 | 29.3 | 29.5 | 27.8 | 27.7 | 27.6 | 27.1 | 25.4 | 29.3 |
| Table 4 Example | (1) | (4) | (6) | (9) | (14) | (15) | (15) | (17) | (22) | (23) | (23) | (26) |
| Polyester acc. to C 1 | 76.3 | 72.4 | — | 72.4 | 70.7 | 70.5 | — | 72.3 | — | 72.9 | — | — |
| Polyester acc. to C 2 | — | — | 72.4 | — | — | — | 72.2 | — | 72.4 | — | 74.6 | 70.7 |
| Notes | All formulation contain a) 30% by weight TiO$_2$/10% by weight Durcal 5, b) 25% by weight TiO$_2$/10% by weight Durcal 5 and in each case 0.5% by weight ACRONAL 4F and benzoin and 0.1% by weight DBTL; the OH/NCO ratio is 1:1 | | | | | | | | | | | |
| Coatings data | | | | | | | | | | | | |
| LT | 60–80 | 70–90 | 65–80 | 65–90 | 60–75 | 65–85 | 70–85 | 55–70 | 60–70 | 70–90 | 60–75 | 55–75 |
| GG 60° ∢ | 42 | 39 | 34 | 52 | 30 | 41 | 35 | 38 | 61 | 35 | 39 | 31 |
| CH | 0 | 0 | 0 | 0 | 0 | 0 | 0 | 0 | 0 | 0 | 0 | 0 |
| EI | 6.8/8.0 | 6.0 | 6.3/7.0 | 5.0/5.3 | 6.1/7.2 | 8.0/9.0 | 7.7/8.9 | 8.2/8.7 | 7.5/8.2 | 7.5 | 8.7/9.2 | 6.8/8.1 |
| Imp. rev. | 115.2 | 115.2 | 115.2 | 115.2 | 115.2 | 115.2 | 115.2 | 115.2 | 230.4 | 115.2 | 230.4 | 115.2 |
| Notes | Curing conditions: 200° C./15–25', 180° C./30' | | | | | | | | | | | |

| | Example D | | | | | | | | | | | |
|---|---|---|---|---|---|---|---|---|---|---|---|---|
| Formulation | 13[a] | 14[b] | 15[a] | 16[b] | 17[oa] | 18[a] | 19[a] | 20[a] | 21[b] | 22[a] | 23[a] | 24[b] |
| Crosslinker acc. to B | 26.9 | 25.1 | 27.9 | 29.3 | 26.1 | 25.6 | — | — | — | — | — | — |
| Table 5 Example | (2) | (7) | (9) | (10) | (11) | (12) | — | — | — | — | — | — |
| Crosslinker acc. to B | — | — | — | — | — | — | 26.6 | 24.2 | 25.1 | 27.8 | 26.9 | 28.6 |
| Table 6 Example | — | — | — | — | — | — | (3) | (5) | (8) | (10) | (11) | (12) |
| Polyester acc. to C 1 | 73.1 | — | 72.1 | 70.7 | — | 74.4 | 73.4 | — | 74.9 | 72.2 | — | 71.4 |
| Polyester acc. to C 2 | — | 74.9 | — | — | 73.9 | — | — | 75.8 | — | — | 73.1 | — |
| Notes | All formulation contain a) 30% by weight TiO$_2$/10% by weight Durcal 5, b) 25% by weight TiO$_2$/10% by weight Durcal 5 and in each case 0.5% by weight ACRONAL 4F and benzoin and 0.1% by weight DBTL; the OH/NCO ratio is 1:1, 0) 1:0.8 | | | | | | | | | | | |
| Coatings data | | | | | | | | | | | | |
| LT | 60–75 | 70–90 | 65–85 | 70–85 | 65–75 | 75–95 | 60–75 | 65–85 | 75–90 | 55–70 | 70–80 | 60–75 |
| GG 60° ∢ | 39 | 68 | 34 | 39 | 55 | 30 | 21 | 31 | 17 | 25 | 49 | 15 |
| CH | 0 | 0 | 0 | 0 | 0 | 0 | 0 | 0 | 0 | 0 | 0 | 0 |
| EI | 5.2/6.1 | 8.1/9.9 | 6.3/6.9 | 5.9/6.7 | 7.5/8.3 | 5.7/7.1 | 3.4/4.5 | 6.8/7.1 | 4.5/6.1 | 5.5/6.9 | 6.5/7.4 | 4.7/5.8 |
| Imp. rev. | 115.2 | 230.4 | 115.2 | 115.2 | 115.2 | 115.2 | 115.2 | 115.2 | 115.2 | 115.2 | 115.2 | 115.2 |
| Notes | Curing conditions: 200° C./15–25', 180° C./30' | | | | | | | | | | | |

What is claimed as new and desired to be secured by Letters Patent of the United States is:

1. A urea- and uretdione-functional polyisocyanate comprising the following formula (I):

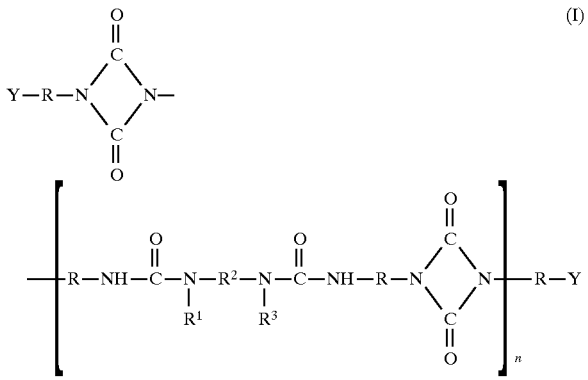

where

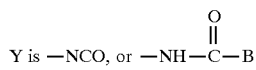

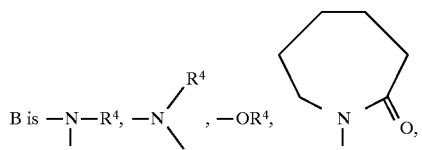

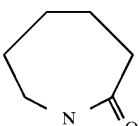

$R^4 = N-O-$ or 1,2,4-triazole;

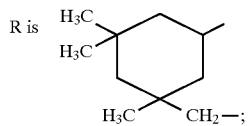

n is an integer of from 1 to 20;

$R^1$, $R^3$ are not more than one linear or branched (cyclo) alkyl radical having 1–14 carbon atoms or H and at least one of the following radicals:

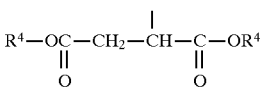

and/or

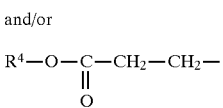

$R^2$ is R, linear or branched (cyclo)alkyl radical having 6 carbon atoms;

$R^4$, $R^5$ are identical or different hydrocarbon radicals having 1 to 14 carbon atoms.

2. The polyisocyanate of claim 1, further comprising:
 a) a content of free NCO groups of $\leq 5$,
 b) an overall NCO content which includes free, and blocked, of from 8 to 16% by weight, and
 c) a varying melting range from 70° to 180° C.

3. The polyisocyanate in claim 1 or 2, further comprising radicals of the reaction products of maleic and/or fumaric ester with diamines selected from the group consisting of 1,2-diaminoethane, 1,3-diaminopropane, 1,4-diaminobutane, 1,5-diaminopentane, 1,6-diaminohexane, 2-methyl-1,5-diaminopentane (DA 51), 2,2,4(2,4,4)-trimethyl-1,6-diaminohexane (TMD), 2,4'- and/or 4,4'-diaminodicyclohexylmethane (HMDA), 1,11-diaminoundecane, 1,12-diaminododecane, 1,4- and/or 1,2-diaminocyclohexane, m-hexahydroxylylenediamine (HXDA), and 1-amino-3,5,5-trimethyl-5-aminomethylcyclohexane isophoronediamine (IPD).

4. The polyisocyanate of claim 3, wherein said radical is diethyl, dibutyl and di-2-ethylhexyl maleate.

5. The polyisocyanate of claim 1, wherein said polyisocyanate is blocked with a compound selected from the group consisting of methanol, ethanol, butanol, 2-ethylhexanol (EHL), dibutylamine (DBA), di-2-ethylhexylamine, methylcyclohexylamine, acetone oxime, methyl ethyl ketoxime, acetophenone oxime, cyclohexanone oxime, caprolactam and 1,2,4-triazole.

6. A process for preparing a urea- and uretdione-functional polyisocyanate having free, or partially or totally blocked isocyanate groups, comprising a reaction with the steps in accordance with the following equation:

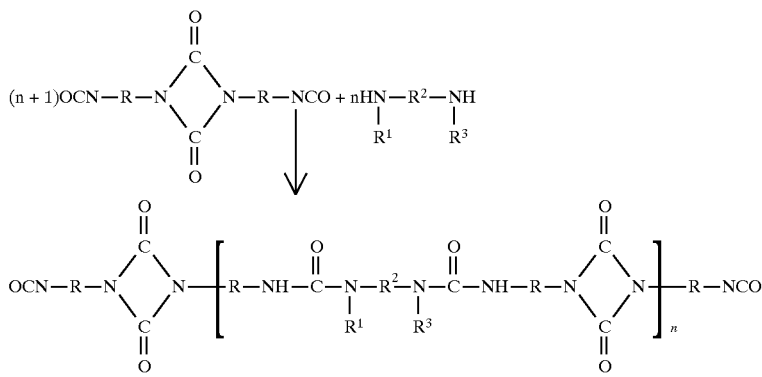

7. The process of claim 6, wherein the reaction takes place in a solvent.

8. The process of claim 6, wherein the reaction is carried out continuously in an intensive compounder without solvent.

9. The process of claim 8, wherein the reaction is carried out in a twin-screw extruder.

* * * * *